United States Patent [19]

Cardis et al.

[11] Patent Number: 4,846,984
[45] Date of Patent: Jul. 11, 1989

[54] LUBRICANT ADDITIVES DERIVED FROM AMINOMERCAPTOTHIADIAZOLE AND LUBRICANT COMPOSITIONS CONTAINING SAME

[75] Inventors: Angeline B. Cardis, Florence; Robert H. Davis, Pitman, both of N.J.; Alfred B. Piotrowski, Philadelphia, Pa.

[73] Assignee: Mobil Oil Corporation, New York, N.Y.

[21] Appl. No.: 189,455

[22] Filed: May 2, 1988

Related U.S. Application Data

[63] Continuation-in-part of Ser. No. 98,338, Sep. 18, 1987, abandoned.

[51] Int. Cl.[4] ............... C10M 135/36; C07D 285/12
[52] U.S. Cl. ................... 252/47.5; 548/136; 548/138; 548/141
[58] Field of Search ............ 252/47.5; 548/141

[56] References Cited

U.S. PATENT DOCUMENTS

| | | | |
|---|---|---|---|
| 3,929,652 | 12/1975 | Seni et al. | 252/47.5 |
| 4,260,501 | 4/1981 | Shini | 252/47.5 |
| 4,301,019 | 11/1981 | Horodysky et al. | 252/47.5 |
| 4,329,475 | 5/1982 | Rothgery | 548/141 |
| 4,456,551 | 6/1984 | Weaver et al. | 548/141 |
| 4,492,793 | 1/1985 | Klenk | 548/141 |
| 4,584,114 | 4/1986 | Gemmill et al. | 252/47.5 |
| 4,587,254 | 5/1986 | Toyojuku et al. | 548/141 |

Primary Examiner—William R. Dixon, Jr.
Assistant Examiner—E. McAvoy
Attorney, Agent, or Firm—Alexander J. McKillop; Charles J. Speciale

[57] ABSTRACT

Disclosed herein is the reaction product of 5-amino-2-mercapto-1,3,4-thiadiazole with hydrocarbyl epoxides. The resulting reaction product finds use as an additive in lubricating oil compositions.

14 Claims, No Drawings

4,846,984

LUBRICANT ADDITIVES DERIVED FROM AMINOMERCAPTOTHIADIAZOLE AND LUBRICANT COMPOSITIONS CONTAINING SAME

This is a continuation-in-part of our co-pending application Ser. No. 098,338, filed on Sept. 18, 1987, now abandonend.

NATURE OF THE INVENTION

This invention relates to the reaction products of an aminomercaptothiadiazole and a hydrocarbyl epoxide. More specifically this invention is concerned with lubricant compositions containing these reaction products.

BACKGROUND OF THE INVENTION

In the lubrication art, zinc dithiophosphates have been utilized as multifunctional lubricant additives to provide antiwear protection as well as to inhibit oxidation of petroleum lubricants. Because of environmental and toxilogical considerations, it is desirable to provide lubricating oil compositions which are ashless and which do not contain phosphrous. Although ashless, non-phosphrous additives have been available in lubricant compositions to provide protection against either engine wear or oxidation of the lubricant, attempts to achieve both with a single additive have generally been unsatisfactory.

U.S. Pat. No. 4,382,869 discloses that reaction products of mercapthothiadiazoles and hydroxyl-containing or borated hydroxyl-containing unsaturated compounds such as oleyl alcohol have been found to be effective multifunctional friction reducing and corrosion inhibiting additives when evaluated in lubricating oils.

SUMMARY OF THE INVENTION

The present invention is directed to novel reaction products of 5-amino-2-mercapto-1,3,4-thiadiazole with hydrocarbyl epoxides and lubricant compositions containing these reaction products.

DETAILED DESCRIPTION OF THE INVENTION

The reaction of the 5-amino-2-mercapto-1,3,4-thiadiazole with hydrocarbyl epoxides is preferably conducted in a molar ratio of between 0.5 and 3.25 moles of hydrocarbyl epoxide to 1 mole of thiadiazole. The reaction is carried out at a temperature between 80° and 200° C. at ambient pressure and preferably is conducted in a non-reactive atmosphere such as a nitrogen gas blanket. The hydrocarbyl epoxide preferably is one in which the average number of carbon atoms in the hydrocarbyl molecule is between 6 and 40 although a range of 12 to 24 carbon atoms is preferred. Ordinarily the reaction will require between 3 and 10 hours for completion. Even more preferred are the alpha-olefin epoxides of between 14 and 20 carbon atoms.

The reaction product is added to the liquid oil composition at a concentration between 0.1 and 5 percent by weight.

Of particular significance, in accordance with the present invention, is the ability of the 5-amino-2-mercapto-1,3,4-thiadiazole and hydrocarbyl epoxide reaction products to improve a variety of properties. They include the improved wear resistance or friction qualities of lubricated parts and the improved resistance to oxidation of oleaginous materials such as lubricating media. These lubricants preferably comprise liquid mineral oil or a synthetic oil or mixtures thereof, but also may be a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 6000 SUS at 100° F., and preferably, from about 50 to about 250 SUS at 210° F. These oils may have viscosity indexes ranging to about 100 or higher preferably from about 70 to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils. Other thickening agents include salt and salt-soap complexes as calcium stearate-acetate (U.S. Pat. No. 2,197,263); barium stearate acetate (U.S. Pat. No. 2,564,561); calcium stearate-caprylate-acetate complexes (U.S. Pat. No. 2,999,065); calcium caprylate-acetate (U.S. Pat. No. 2,999,066); and calcium salts and soaps of low-, intermediate- and high-molecular weight acids and of nut oil acids. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified inn a butyl-substituted bis(p-phenoxy phenyl) ether, phenoxy phenylethers.

It is to be understood that the compositions contemplated herein can also contain other materials. For example, corrosion inhibitors, extreme pressure agents, antiwear agents, defoamants, detergents, dispersants, and the like can be used. These materials do not detract from the value of the compositions of this invention. Rather the materials serve to impart their customary properties to the particular compositions in which they are incorporated.

The following examples illustrate the preparation of the reaction products of this invention and their use in lubricating oil compositions.

EXAMPLES

Example 1

Thirteen and three-tenths grams (13.3 g) of 2-amino-5-mercapto-1,3,4-thiadiazole and 50.0 grams of $C_{16}$ hydrocarbyl epoxide were stirred under nitrogen at 130° C. for three hours, at which point a clear solution was obtained. The temperature of the reaction mixture (130° C.) was maintained for an additional three hours. The mixture was then vacuum topped at 170° C. A negligible amount of material was removed. The resulting product was light yellow in color and had a waxy appearance.

Example 2

A mixture of $C_{14}$–$C_{20}$ hydrocarbyl epoxides (259grams) and 66.6 grams of the same aminomercaptothiadiazole were heated and stirred under nitrogen at 80° C. for two hours and then at 120° C. for one hour. The temperature was then increased to 180° C. and maintained for three hours. The resulting product was a dark viscous fluid very soluble in oil.

Example 3

A mixture of $C_{14}$–$C_{20}$ hydrocarbyl epoxides (388.5 grams) and 66.6 grams of the same aminomercaptothiadiazole used in the preceding examples were heated and stirred under nitrogen at 130°–140° C. for three hours. The reaction product was tan and waxy.

Example 4

Two hundred and forty (240) grams of C-16 hydrocarbyl epoxides and the same aminomercaptothiadiazole were heated with stirring under nitrogen for three hours at 180° C.

Example 5

Fifty three (53) grams of a mixture of C-14 hydrocarbyl epoxides and 33 grams of the aminomercaptothiadiazole were heated with stirring under nitrogen at 130° C. for three hours. An additional portion of epoxide (53g) was added and heating was continued an additional three hours at 130° C.

The products described above were blended in a concentration of 1.5 weight percent. in mineral oil and tested in a Shell four-ball wear tester. The results presented in Table 1 demonstrate the antiwear protection afforded by these products.

TABLE 1

| Example | Temp., °F. | Wear Scar Diameter (mm) | |
|---|---|---|---|
| | | 1000 rpm | 2000 rpm |
| Base Stock | 200 | 0.65 | 3.26 |
| | 300 | 1.71 | 2.34 |
| 2 | 200 | 0.69 | 2.03 |
| | 300 | 0.72 | 1.86 |
| 3 | 200 | 1.57 | 2.19 |
| | 300 | 1.53 | 2.08 |
| 4 | 200 | 0.66 | 0.87 |
| | 300 | 0.74 | 1.99 |
| 5 | 200 | 0.55 | 0.75 |
| | 300 | 0.80 | 2.00 |

The product of Example 1 was blended at 1.0 weight percent in an ashless, phosphorus-free heavy circulating oil formulation. This fully formulated oil was evaluated in comparison with a reference oil, containing 1.0 weight percent of a commercial zinc dithiophosphate. The formulated oil containing neither zinc dithiophosphate nor the product of Example 1 was also tested. Evaluation for oxidative stability was carried out by bubbling air through the oil at a rate of 5 liters per hour at 325 ° F. for 40 hours Present in the composition were samples of metals commonly used in engine construction, namely, iron, copper, aluminum and lead. See U.S. Pat. No. 3,682,980, incorporated herein by reference for further details of the test. Reductions in viscosity-increase or limiting of neutralization number (or both) show effective control. The formulation was also tested for gear wear protection according to the FZG Gear Test (DIN-51.354). In this test, dip-lubricated gears are weighed and operated at a fixed speed and fixed initial oil temperature (90 ° C.) in the gear oil under test. The load on the teeth is increased in increments. After each load stage, the weight changes are determined and recorded. The higher the Fail Stage value the better the material. A lower the wear value corresponds to a better product. Details of this test are further provided in U.S. Pat. No. 4,661,273 incorporated herein by reference. The results in Table 2 show that the products herein described effectively possess both the antiwear/load carrying and the oxidation inhibiting properties of zinc dithiophosphates.

TABLE 2

| Oil Sample | FZG Fail Stage | TAN | % Viscosity Increase |
|---|---|---|---|
| Ref. with 1.0% Zn (DTP)$_2$ | 13 | 2.87 | 38 |
| Ref. less Zn (DTP)$_2$ | 9 | 6 | 45 |
| With 1.0% of Example 1 | 13 | 4.1 | 35 |

We claim:

1. The reaction product obtained by reacting 5-amino-2-mercapto-1,3,4-thiadiazole with an hydrocarbyl epoxide or mixture of hydrocarbyl epoxides at a temperature of between about 80° and about 200° C., a molar ratio of hydrocarbyl epoxide compound to thiadiazole of between about 0.5 and about 3.25, the hydrocarbyl epoxide having been prepared from an olefin having an average number of carbon atoms per molecule of between about 6 and about 40.

2. A lubricant composition comprising a lubricating component and a means for enhancing the antiwear quality and antioxidant quality of the oil comprising the reaction product of claim 1.

3. The lubricant composition of claim 2 wherein said means for enhancing comprises a minor amount of a compound produced by the reaction of 5-amino-2-mercapto-1,3,4-thiadiazole with a hydrocarbyl epoxide.

4. The lubricant composition of claim 2 wherein the hydrocarbyl epoxide has an average number of carbon atoms per molecule of between about 14 and about 20.

5. The composition of claim 2 wherein the lubricating component is selected from the group consisting of mineral oil, synthetic oil, mixtures thereof, and greases.

6. A lubricant composition comprising a liquid lubricant and between about 0.1 and about 5 percent by weight of the total composition of an additive produced by the reaction of 5-amino-2-mercapto-1,3,4-thiadiazole with a hydrocarbyl epoxide at a temperature between about 80° and about 200° C., and a molar ratio of hydrocarbyl epoxide compound to thiadiazole between about 0.5 and about 3.25, the hydrocarbyl epoxide having been prepared from an olefin having an average number of carbon atoms per molecule of between about 6 and about 40.

7. The lubricant composition of claim 6 wherein the lubricant is selected from the group consisting of mineral oil, synthetic oil, mixtures thereof, and greases.

8. A method for making a lubricant composition comprising adding to a major proportion of a lubricant between about 0.1 and about 5 percent by weight of the total composition of the reaction product obtained by reacting 5-amino-2-mercapto-1,3,4-thiadiazole with a hydrocarbyl epoxide or mixture of hydrocarbyl epoxides at a temperature between about 80° and about 200° C., a molar ratio of hydrocarbyl epoxide compound to thiadiazole of between about 0.5 and about 3.25 the hydrocarbyl epoxide having been prepared from an olefin having an average number of carbon atoms per molecule of between about 6 and about 40.

9. The method of claim 8 wherein the lubricant is selected from the group consisting of mineral oil, synthetic oil, mixtures thereof, and grease.

10. A lubricant composition comprising a lubricating component and between about 0.1 and about 5 percent by weight of the total composition of an additive for enhancing the antiwear and antioxidant quality of the lubricating component comprising the reaction product obtained by reacting 5-amino-2-mercapto-1,3,4-thiadiazole with an alpha-olefin epoxide or mixture of alpha-olefin epoxides, the alpha-olefin epoxide having an average number of carbon atoms per molecule of between about 14 and about 20 reacted at a temperature between about 80° and about 200° C., and a molar ratio of epoxide compound to thiadiazole between about 0.5 and about 3.25.

11. The lubricant composition of claim 10 wherein the lubricating component is selected from the group consisting of mineral oil, synthetic oil, mixtures thereof, and greases.

12. The lubricant composition of claim 10 wherein said additive for enhancing comprises a minor amount of a compound produced by the reaction of 5-amino-2-mercapto-1,3,4-thiadiazole with an alpha-olefin epoxide.

13. A method for making a lubricant composition comprising adding to a major proportion of a lubricant between about 0.1 and about 5 percent by weight of the total composition of the reaction product obtained by reacting 5-amino-2-mercapto-1,3,4-thiadiazole with an alpha-olefin epoxide or mixture of alpha-olefin epoxides wherein the alpha-olefin epoxide has an average number of carbon atoms per molecule of between about 14 and 20 reacted at a temperature between about 80° and about 200° C. and a molar ratio of epoxide compound to thiadiazole between about 0.5 and about 3.25.

14. The method of claim 13 wherein the lubricant is selected from the group consisting of mineral oil, synthetic oil, mixtures thereof, and grease.

* * * * *